United States Patent
Suarez-Rivera et al.

(10) Patent No.: US 9,995,698 B2
(45) Date of Patent: Jun. 12, 2018

(54) INTEGRATED ANALYSIS OF PORE FLUIDS FOR CHARACTERIZATION OF RESERVOIR POTENTIAL

(71) Applicant: W. D. Von Gonten Laboratories LLC, Houston, TX (US)

(72) Inventors: Roberto Suarez-Rivera, Houston, TX (US); William D. Von Gonten, Houston, TX (US); Kelly Vaughn, Hockley, TX (US); Ryan Zak, Cypress, TX (US)

(73) Assignee: W.D. Gonten Laboratories LLC, Houston, TX (US)

(*) Notice: Subject to any disclaimer, the term of this patent is extended or adjusted under 35 U.S.C. 154(b) by 0 days. days.

(21) Appl. No.: 15/298,734

(22) Filed: Oct. 20, 2016

(65) Prior Publication Data

US 2017/0138872 A1    May 18, 2017

Related U.S. Application Data

(60) Provisional application No. 62/243,751, filed on Oct. 20, 2015.

(51) Int. Cl.
| | |
|---|---|
| *G01N 25/02* | (2006.01) |
| *G01N 33/24* | (2006.01) |
| *E21B 49/02* | (2006.01) |
| *E21B 49/08* | (2006.01) |
| *E21B 43/26* | (2006.01) |

(52) U.S. Cl.
CPC .............. *G01N 25/02* (2013.01); *E21B 49/02* (2013.01); *E21B 49/08* (2013.01); *G01N 33/24* (2013.01); *E21B 43/26* (2013.01)

(58) Field of Classification Search
CPC .......... E21B 43/26; E21B 49/02; E21B 49/08; G01N 25/02; G01N 33/24
USPC ....... 436/25, 31, 32, 60, 139, 143, 155, 157, 436/178, 181; 422/78
See application file for complete search history.

(56) References Cited

PUBLICATIONS

Labus et al. Journal of Petroleum Science and Engineering, vol. 127, Feb. 14, 2015, pp. 482-489.*
Luffel, D.L. and Guidry, F.K., 1989. Reservoir Rock properties of Devonian Shale from Core and Log Analysis. SCA International Symposium on Core Analysis. Dallas, Texas, vol. 1, No. 8910.
Spears, R.W. Dudus, D. Foulds, A. Passey Q. Siinha, and W.L. Esch 2011. Shale Gas Core Analysis: Strategies for Normalizing between Laboratories and a Clear Need for Standard Materials, presented at the SPWLA 52nd Annual Logging Symposium, May 14-18, Colorado Springs, CO.
Handwerger, D.A., Suarez-Rivera R., Vaughn, K. I. et al. 2011. Improved Petrophysical Core Measurements on Tight Shale Reservoirs Using Retort and Crushed Samples. Paper SPE147456 presented at SPE Annual Technical Conference and Exhibition, Denver, Colorado, Oct. 30-Nov. 2.
D.A. Handwerger; D. Willberg; M. Pagels; B. Rowland, and J.F. Keller. 2012. Reconciling Retort versus Dean Stark Measurements on Tight Shales. SPE 159976 presented at the SPE Annual Technical Conference and Exhibition held in San Antonio, Texas, USA, Oct. 8-10, 2012.
Pallatt, N. and D. Thornley 1990. The role of bound water and capillary water in the evaluation of porosity in reservoir rocks. Symposium on Core Analysis. London, U.K., vol. 1, No. 90012, 15 p.
D. A. Handwerger, J. Keller, K. Vaughn, 2011. Improved Petrophysical Core Measurements on Tight Shale Reservoirs Using Retort and Crushed Samples. SPE-147456-MS presented at the SPE Annual Technical Conference and Exhibition, Oct. 30-Nov. 2, Denver, Colorado, USA.
T. Jiang, E. Rylander, P. M. Singer, R.E. Lewis, S. M. Sinclair. Integrated Petrophysical Interpretation of Eagle Ford Shale with 1-D and 2-D Nuclear Magnetic Resonance (NMR). 2013. SPWLA-2013-LL presented SPWLA 54th Annual Logging Symposium, Jun. 22-26, New Orleans, Louisiana.
M. Labus, K. Labus and P. Bujok. 2015. Thermal Methods Implementation in Porosity Determination of Shale Rocks. Presented at the 77th EAGE Conference and Exhibition 2015. (also Determination of the pore space parameters in microporous rocks by means of thermal methods. Journal of Petroleum Science and Engineering. vol. 127, Mar. 2015, pp. 482-489).
Konoshonkin, D V; Parnachev, S V, 2015. Existing approaches to tight rock laboratory petrophysics: a critical review. IOP Conference Series: Earth and Environmental Science, vol. 24, No. 1, 2015, pp. 12042-12052(11).
Simpson G. and N. S. Fishman 2015. Unconventional Tight Oil Reservoirs: A Call for New Standardized Core Analysis Workflows and Research. SCA2015-022. Presented at the International Symposium of the Society of Core Analysts held in St. John's, Newfoundland and Labrador, Canada, Aug. 16-21.

(Continued)

*Primary Examiner* — Maureen Wallenhorst
(74) *Attorney, Agent, or Firm* — Jonathan M. Pierce; Porter Hedges LLP (57) ABSTRACT

Disclosed is a method and system for integrating measurements from known laboratory techniques of fluid extraction (Dean Stark, Retort, Rock-Eval), which conducted independently by multiple disciplines and which have been so far treated as independent evaluations. In using these results, particularly Dean Stark and Retort, the oil industry has shown specific preferences between these two methods, with some groups advocating the validity of one method over the other, and others showing the opposite. Forums and discussions have been organized by the technical community to debate the benefits and drawbacks of each of these and to define which is the more suitable for reservoir characterization. Commercial laboratories have specialized in one method or the other based on their perceived validity. Both methods are correct, but each measure an incomplete assessment of the properties needed, and that together they provide considerable more information than when considered independently.

10 Claims, 10 Drawing Sheets

(56) References Cited

PUBLICATIONS

Ringen J.K., C. Halvorsen, K.A. Lehne, H. Rueslaatten, and H. Holand 2001. Reservoir Water Saturation Measured on Cores; Case Histories and Recommendations. 6th Nordic Symposium on Petrophysics, May 15-16, Trondheim, Norway.

Nicot B, N. Vorapalawut, B. Rousseau, L. Madariaga, G. Hamon, and J.P. Korb 2015. Estimation Saturations in Organic Shales Using 2D NMR. Presented at the International Symposium of the Society of Core Analysts held in St. John's Newfoundland and Labrador, Canada, Aug. 16-21.

Luffel D.L. and F.K. Guidry 1992. New Core Analysis Methods for Measuring Reservoir Rock Properties of Devonian Shale. SPE-20571-PA. Journal of Petroleum Technology vol. 44, No. 11, November.

Sondergeld, C.H., K.E. Newsham, J.T. Comisky, M.C. Rice, and C.S. Rai 2010. Petrophysical Considerations in Evaluating and Producing Shale Gas Resources. SPE 131768. Presented at the SPE Unconventional Gas Conference, Feb. 23-25, Pittsburg, Pennsylvania, USA.

Behar F., V. Beaumont, and De.B. Penteado 2001. Rock-Eval 6 Technology: Performances and Developments. Oil and Gas Science and Technology—Rev. IFP, vol. 56, No. 2, pp. 111-134.

Holman A.I., K. Grice, C.M.B. Jaraula, A. Schimmelmann, and J.J. Brocks 2012. Efficiency of extraction of polycyclic aromatic hydrocarbons from the Paleoproterozoic Here's Your Chance Pb/Zn/Ag ore deposit and implications for a study of Bitumen II. Organic Geochemistry 52, 81-87.

Roberto Suarez-Rivera, W.D. Von Gonten, K. Vaughn, R. Zak, E. Carter, A. Kurup, N. Nelson, D. Hajek, and M. Shaw 2016. Integration of Thermal and Solvent Extraction Methods for Improved Characterization of Hydrocarbon in Place and Producibility. Unconventional Resources Technology Conference held in San Antonio, Texas, USA, Aug. 1-3, 2016.

Presentation at the Unconventional Resources Technology Conference held in San Antonio, Texas, USA, Aug. 1-3, 2016.

* cited by examiner

| Alkane | Formula | Boiling point [°C] |
|---|---|---|
| Methane | $CH_4$ | −162 |
| Ethane | $C_2H_6$ | −89 |
| Propane | $C_3H_8$ | −42 |
| Butane | $C_4H_{10}$ | 0 |
| Pentane | $C_5H_{12}$ | 36 |
| Hexane | $C_6H_{14}$ | 69 |
| Heptane | $C_7H_{16}$ | 98 |
| Octane | $C_8H_{18}$ | 126 |
| Nonane | $C_9H_{20}$ | 151 |
| Decane | $C_{10}H_{22}$ | 174 |
| Undecane | $C_{11}H_{24}$ | 196 |
| Dodecane | $C_{12}H_{26}$ | 216 |
| Hexadecane | $C_{16}H_{34}$ | 287 |
| Icosane | $C_{20}H_{42}$ | 343 |
| Triacontane | $C_{30}H_{62}$ | 450 |
| Tetracontane | $C_{40}H_{82}$ | 525 |
| Pentacontane | $C_{50}H_{102}$ | 575 |
| Hexacontane | $C_{60}H_{122}$ | 625 |

INTEGRATED ANALYSIS OF PORE FLUIDS FOR CHARACTERIZATION OF RESERVOIR POTENTIAL

CROSS-REFERENCE TO RELATED APPLICATIONS

This application claims priority to U.S. Provisional Application Ser. No. 62/243,751 filed on Oct. 20, 2015, which is incorporated herein by reference.

FIELD OF THE INVENTION

The disclosure relates to techniques for extracting pore fluids from unconventional, tight, organic-rich mudstone reservoirs, for evaluation of fundamental reservoir properties of porosity and saturations.

This disclosure defines a method and a workflow for integrating two known, but previously mutually exclusive, techniques into a single solution, based on the discovery that the two methods are measuring different but supplementary volumes of the pore space. By using an integrated solution, one can provide a better and more robust characterization of the real reservoir properties. Furthermore, there is one other methodology for evaluating hydrocarbon fluid volumes that is common to geochemistry and source rock characterization: Rock-Eval pyrolysis. This methodology is also a thermal extraction methodology and in this disclosure, this third mutually exclusive technique can also be directly integrated with the previous. To our knowledge, there has not been a public study or reference that integrates these various methods and shows them not as competing alternatives but as incomplete supplementary methods, that support each other, and together provide a better characterization of reservoir quality and potential.

BACKGROUND

Because of the complex nature (heterogeneity, small porosity, and nano-Darcy permeability) of rocks in unconventional reservoirs, traditional methods of measuring porosity and saturations do not work. Thus starting in the early 1980's, a number of methods were tested and proposed for evaluation of unconventional reservoirs. The two more common methods are: thermal extraction of pore water and hydrocarbons (Retort), and solvent extraction of pore water and hydrocarbons (Dean Stark). The gas-filled volume is measured by pycnometry and following Boyle's law of gasses. By adding the measured volumes of the extracted water, oil, and gas, the pore volume in the rock may be obtained, and therefore the total porosity ($\Phi$). The fraction of this porosity filled with gas, water, and oil are the gas, water, and oil pore fluid saturations ($S_g$, $S_w$, $S_o$).

A problem arises because the volumes of oil that are measured by Retort or inferred (by weight loss) by Dean Stark do not coincide. This leads to differences in the calculated $\Phi$, $S_g$, $S_w$, $S_o$, and thus in the characterization of the reservoir properties.

There are multiple publications on reservoir characterization and the evaluation of unconventional reservoir properties of porosity and pore fluid saturations using solvent extraction and thermal extraction of pore fluids. However, these methods are treated as independent and exclusive of each other.

Geochemical analysis of organic richness and maturation of source rocks are commonly conducted using pyrolysis (Rock-Eval, Rock-Eval 6, HAWK, or equivalent), using a programmed temperature heating of the samples, in an inert atmosphere, to define the free hydrocarbons present in the sample and the products associated with the cracking of heavy hydrocarbon components, including kerogen. This method, common to the geochemistry community, has not been previously integrated as a supplementary method for evaluating pore volumes and saturations or as an equivalent method to Retort analysis. For convenience in this description, we refer to geochemical pyrolysis as Rock-Eval, but geochemical pyrolysis may alternatively include equivalent systems and methods for geochemical pyrolysis.

A literature search of relevant articles outlining the three methods is provided below. Some references were written with the specific objective to compare and contrast the thermal extraction method versus the solvent extraction method. Please notice however that, even in these references, the two methods are treated as independent from each other, not supplementary to each other. Rock-Eval is typically not mentioned and is considered as a separate evaluation used for geochemical evaluation.

Luffel, D. L. and Guidry, F. K., 1989. Reservoir Rock properties of Devonian Shale from Core and Log Analysis. SCA International Symposium on Core Analysis. Dallas, Texas, vol. 1, no. 8910.

Spears, R. W. Dudus, D. Foulds, A. Passey Q. Sinha, and W. L. Esch 2011. Shale Gas Core Analysis: Strategies for Normalizing between Laboratories and a Clear Need for Standard Materials, presented at the SPWLA $52^{nd}$ Annual Logging Symposium, 14-18 May, Colorado Springs, Colo.

Handwerger, D. A., Suarez-Rivera R., Vaughn, K. I. et al. 2011. "Improved Petrophysical Core Measurements on Tight Shale Reservoirs Using Retort and Crushed Samples. Paper SPE147456 presented at SPE Annual Technical Conference and Exhibition, Denver, Colo., 30 October-2 November.

D. A. Handwerger; D. Willberg; M. Pagels; B. Rowland, and J. F. Keller. 2012. Reconciling Retort versus Dean Stark Measurements on Tight Shales. SPE 159976 presented at the SPE Annual Technical Conference and Exhibition held in San Antonio, Tex., USA, 8-10 Oct. 2012.

Pallatt, N. and D. Thornley 1990. The role of bound water and capillary water in the evaluation of porosity in reservoir rocks. Symposium on Core Analysis. London, U.K., vol. 1, no. 90012, 15 p.

D. A. Handwerger, J. Keller, K. Vaughn, 2011. Improved Petrophysical Core Measurements on Tight Shale Reservoirs Using Retort and Crushed Samples. SPE-147456-MS presented at the SPE Annual Technical Conference and Exhibition, 30 October-2 November, Denver, Colo., USA.

T. Jiang, E. Rylander, P. M. Singer, R. E. Lewis, S. M. Sinclair. Integrated Petrophysical Interpretation of Eagle Ford Shale with 1-D and 2-D Nuclear Magnetic Resonance (NMR). 2013. SPWLA-2013-LL presented SPWLA 54th Annual Logging Symposium, 22-26 June, New Orleans, La.

M. Labus, K. Labus and P. Bujok. 2015. Thermal Methods Implementation in Porosity Determination of Shale Rocks. Presented at the 77th EAGE Conference and Exhibition 2015. (also Determination of the pore space parameters in microporous rocks by means of thermal methods. Journal of Petroleum Science and Engineering. Volume 127, March 2015, Pages 482-489).

Konoshonkin, D V; Parnachev, S V, 2015. Existing approaches to tight rock laboratory petrophysics: a critical review. IOP Conference Series: Earth and Environmental Science, Volume 24, Number 1, 2015, pp. 12042-12052(11).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The disclosure relates to a method and workflow for integrating existing measurements of pore-fluids volumes, pore fluids saturations, and porosity, for a more complete and efficient characterization of reservoir potential. The existing methods were previously used in isolation from one another and in general, they are presented as mutually exclusive alternatives to one another. Multiple hours of public scientific discussions have been spent, and multiple papers have been written promoting one method versus the other and showing the deficiencies of one method versus the other. The industry has opted by choosing one of the other; with the understanding that obtaining consistent results by using the same method is a better option than obtaining different results from each method. The method and workflow of this disclosure also explain what the limitations of each of the stand-alone methods are and how increased information and increased confidence in the results is obtained by integrating them. The method is primarily applicable to organic-rich, unconventional mudstone reservoirs, but is also applicable to other tight and heterogeneous formations requiring fluid extraction methods for evaluation of pore volume, porosity, and saturations. The method addresses understanding the complex surface forces that bound the pore fluids (hydrocarbons of various molecular weights, including bitumen, and brines or various saline concentrations) to the rock solid constituents (clay minerals, non-clay minerals, and organic matter). As a consequence, extracting these fluids from the pore space requires multiple levels of energy (thermal or chemical or both), to overcome the multiple bounding surface forces tying the pore fluids to the rock. In turn, at the same level of energy (supplied either thermally or chemically—using solvents), the same quantity of fluids (water and oil) would be extracted. Thus, differences observed between thermal extraction, and solvent extraction methods are simply a function of differences in the supplied energy. Once the relation between the two energy levels is established, the extraction can be made identical (for brines).

Figure 1:
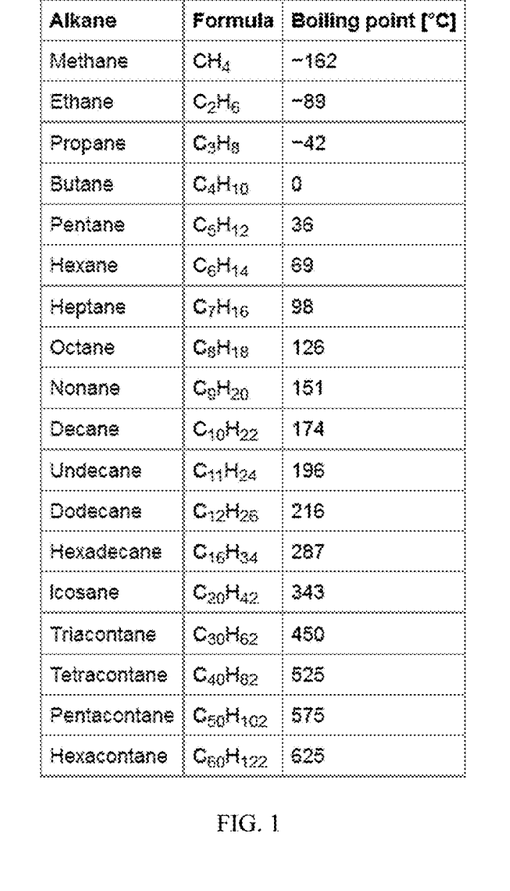
FIG. 1 is an example table of boiling points for alkanes in the range from C1 to C60.

Furthermore, the method and workflow of the disclosure may rely on an understanding of the processes of thermal evaporation, thermal distillation, and thermal cracking, to predict the different chemical transformations occurring when an organic-rich crushed sample is subjected to either temperature or organic solvents. The method is not limited to crushed rock analysis. Crushed rock may be used to increase the surface area and reduce the time required for the measurements. However, there is no inherent limitation in using crushed samples to the applicability of the method. Distillation is a process of separating hydrocarbon components from a hydrocarbon mixture by selective evaporation at increasing temperatures, and subsequent condensation. Given that individual hydrocarbon components in the mixture have different boiling points, these can be evaporated sequentially by increasing the temperature to their required level. For example, FIG. 1 shows an example table of boiling points for alkanes in the range from C1 to C60. The table in FIG. 1 indicates that the light hydrocarbon components (C1 to C5) evaporate readily at room temperature and are typically lost from the samples. The table in FIG. 1 also indicates that distillation of a hydrocarbons mixture that includes light to heavy components (C5 to C60) requires a range of temperatures from 36° C. (C5) to 625° C. (C60). As a reference to the temperature requirements for boiling the high molecular weight constituents: measurements of bitumens from Utah and the bituminous hydrocarbons in Venezuela and Canada indicate boiling points of 535° C.

However, solid organic matter (Kerogen and coke) is also present in the rock samples, and at temperatures in the range from 300° C. to 600° C., kerogens start cracking, and thus transforming their complex molecular structures, and releasing low molecular weight hydrocarbons. Unfortunately, this temperature range overlaps with the distillation temperature of the moderate to heavier hydrocarbons (C20 to C60). Thus, when using thermal methods of fluid extraction, these limitations should be well understood. Cracking temperatures for kerogens depend on the maceral types, and their degree of thermal maturation (Tmax), and these may change from sample to sample. (The process of boiling high molecular weight hydrocarbons and cracking kerogen leaves additional non-soluble residue, which increases the initial coke content in the sample).

In contrast to thermal fluid extraction, solvent extraction removes all hydrocarbon components that are soluble in organic solvents (including bitumen). The ranges of hydrocarbon constituents that can be extracted in this manner depend on the strength of the solvent, its boiling temperature, and the exposure time. All of these are controllable under laboratory conditions, thus, by understanding these ranges and limitations, a better determination of the hydrocarbon constituents can be made, as will be explained below.

The method includes changes in the above boiling points associated to pore-size distributions (Kelvin relationship) and developing relationships to define the proper levels of temperature and solvent schedule to make these measurements compatible with each other. One consequence of this method is that a more detailed and complete analysis of pore fluid constituents in the pore space is provided. A second consequence is that we show that these well-known methods are not stand alone and redundant to one another, but instead they supplement each other. Finally, we show that important decisions of reservoir potential and the appropriate landing of laterals for increasing well production can be made with higher confidence when the results of this method are used.

In an embodiment, a method for integrating Dean Stark and Retort, two known but previously mutually exclusive, techniques into a single solution is disclosed. The method can also include integrating Rock-Eval technique or any equivalent geochemical pyrolysis technique to the above. The method can include conducting tests on the various thermal extraction and solvent extraction instruments (e.g., Retort, Thermo Gravimetric Analysis (TGA), Rock-Eval, Rock-Eval 6, Hawk, Dean Stark, Karl Fisher, and Accelerated Solvent Extraction (ASE) using reference samples. The method can include outputting results from all measurements as extracted volume (in cc) per 100 gr of rock or expressed as fractions of the bulk rock volume (%). The method can include evaluating results and validate the equivalence between water measurements, oil measurements and, solid carbon measurements, at the corresponding temperature limits. The method can include evaluating the relationship between the above using a linear fit regression, define the confidence interval and conduct error propagation analysis. The method can include using the above results to properly calibrate the various instruments and to obtain identical results. The method can include using the above results and calibrations to define an integrated evaluation of reservoir properties, using the following model:

Organic carbon: TOC=(Liquid Hydrocarbon Components+Bitumen_1+Bitumen_2+Kerogen+Dead Carbon)

Water: Total water=(Loosely Bound Water+Strongly Bound Water+Structural Water)

Oil: Light molecular weight hydrocarbons (C1-C10)+Intermediate molecular weight hydrocarbons (C10-C20)+Heavier molecular weight hydrocarbons including bitumen (>C20)

Loosely bound water=Retort or TGA water at T≤T1=120 deg C.

Strongly bound water=Retort or TGA water at T1=120 deg C.≤T≤T2=300 deg C.

Total Pore Water=(Loosely bound+Strongly bound water)=Solvent extraction water: Dean Stark water or Karl Fischer water Structural water=Retort or TGA water at T2=300 deg C.≤T≤T3=650 deg C.

Low molecular weight hydrocarbons=Retort or TGA hydrocarbons at T≤T1=120 deg C.

Intermediate molecular weight hydrocarbons=Retort T2 or Rock-Eval S1 hydrocarbons at T≤300 deg C.

Higher molecular weight hydrocarbons=Solvent extracted hydrocarbons (Dean Stark, ASE)−(Low+Intermediate molecular weight hydrocarbons)

Total liquid hydrocarbons including Bitumen_1=Solvent extracted hydrocarbons (Dean Stark, ASE)

Oil Prone Kerogen+Bitumen_2=(Retort Oil T≤650 deg C.−Dean Stark Oil).

Oil and Gas Prone Kerogen+Bitumen_2=(Rock-Eval S2 Oil T≤=650 deg C.−Dean Stark Oil).

Gas Prone Kerogen=(Retort Oil T≤T3=650 deg C.).

Solid Carbon+Bitumen_2=(Rock-Eval TOC−Dean Stark).

In an embodiment, a computer readable storage medium storing instructions for integrating Dean Stark and Retort, two known but previously mutually exclusive, techniques into a single solution is disclosed. The instructions for integrating Dean Stark and Retort can also include integrating Rock-Eval pyrolysis and TGA techniques to the above.

In an embodiment, a system is disclosed for integrating Dean Stark and Retort, two known but previously mutually exclusive, techniques into a single solution are disclosed. The system for integrating Dean Stark and Retort can also include integrating Rock-Eval pyrolysis and TGA techniques to the above.

BRIEF DESCRIPTION OF THE DRAWINGS

For a more detailed description of the embodiments of the disclosure, reference will now be made to the accompanying drawings, wherein.

DEFINITIONS

Formation: Subterranean body of rock that is sufficiently distinctive and continuous. This could be a reservoir or non-reservoir region.

Reservoir: A formation that contains sufficient volume hydrocarbons in its void (porous) space, and has sufficient permeability to allow the production of the contain hydrocarbon Reservoir quality: Set properties of the reservoir rock that define its quality in relation to hydrocarbon in place (e.g., hydrocarbon filled porosity, effective porosity, organic content, degree of maturation, others) and the potential hydrocarbon mobility (permeability, hydrocarbon viscosity, hydrocarbon gas oil ratio, reservoir pressure, others)

Well production: Total volume of hydrocarbons produced from a well. This is typically directly proportional to the amount of created surface area in contact with the reservoir.

Reservoir properties: Also referred as petrophysical reservoir properties, refers to properties that define the hydrocarbon storage capacity and hydrocarbon production potential and typically consist of bulk density, grain density, porosity, pore fluid saturations (gas, water, and oil), and permeability.

Laboratory samples: These are small sample plugs or crushed and sieved rock material obtained from deep earth cores, representing the zones of interest.

Solvent extraction: These are methods for pore fluid extraction from tight rocks based on exposure to solvents. Various types and cycles of solvents are used, based on their affinity to water, salts, and hydrocarbons. The most common solvent extraction method is the Dean Stark method.

Thermal extraction: These are methods for pore fluid extraction from tight rocks based on vaporization, distillation and hydrocarbon cracking under temperature. Various temperature schedules are used. The most common thermal extraction method is the Retort method.

Karl Fischer: A solvent extraction method that uses anhydrous methanol as a solvent for efficiently extracting water and measuring this extracted water with high precision based on coulometric titration.

Thermal Gravimetric Analysis (TGA): A thermal extraction method that uses high precision balance and oven to subject the sample to controlled temperature schedules and measure accurately the loss of sample weight as the pore fluids (water and hydrocarbons) are extracted by evaporation, distillation and cracking.

Rock-Eval Pyrolysis: A thermal extraction method common in basic geochemistry analysis that uses temperature and controlled environments (non-oxic and oxic) to extract hydrocarbons from laboratory samples by evaporation, distillation and cracking.

Accelerated Solvent Extraction (ASE): This is a new method of solvent extraction that uses automation, multiple cycles, and high temperature and pressure conditions, for controlled extraction of hydrocarbons from crushed and non-crushed rock samples.

Distillation: Distillation is a process of separating hydrocarbon components from a hydrocarbon mixture by selective evaporation and condensation. The process exploits differences in boiling points of the components in the mixture.

Cracking: Cracking is the process of breaking long-chain, complex hydrocarbons into short ones. For example kerogens or heavy hydrocarbons are broken down into simpler, light hydrocarbons molecules. The rate of cracking and the end products are strongly dependent on the temperature, and presence of catalysts.

Calibration: Calibrating temperature limits at which a thermal extraction instrument operates means that the temperature limits 120 deg C., 300 deg C. or 650 deg C. is adjusted (for example within 10 deg C. to 50 deg C.) so that a measurement of at least one of water amount, oil amount and, solid carbon amount matches an equivalent measurement performed using another thermal extraction instrument, or a solvent extraction instrument. Only one temperature limit may be calibrated.

DETAILED DESCRIPTION

In the following description, numerous details are set forth to provide an understanding of the disclosure. However, it will be understood by those skilled in the art that the disclosure may be practiced without these details and that numerous variations or modifications from the described embodiments are possible.

The disclosure relates to techniques to improve and/or optimize reservoir characterization. It was developed specifically for unconventional reservoirs, but it applies broadly to all tight reservoirs, including source rocks, tight sands, heterogeneous tight reservoirs and other systems that rely on the use of thermal extraction or/and solvent extraction methods for evaluating pore fluid volumes, porosity, and/or saturations. The disclosure relates to the realization that solvent extraction and thermal extraction methods measure different fractions of the pore fluids and thus are complementary of each other and not redundant to one another as previously assumed. The disclosure relates to a method and workflow for making the integration of these different measurements possible, and for obtaining an advanced, more complete, and more robust characterization of reservoir properties, reservoir quality, and reservoir potential. The method of the disclosure, when used in connection with the disclosure of provisional U.S. patent application Ser. No. 62/152,167, entitled Lateral Placement and Completion Design for Improved Well Performance of Unconventional Reservoirs and incorporated herein by reference, provides additional information to supplement the selection of optimal lateral well landing points and improves the potential for better placement and higher well production.

Figure 2:
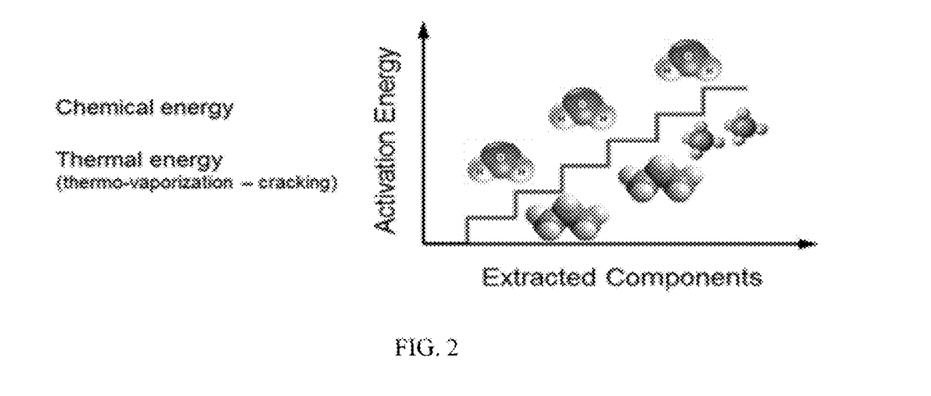
FIG. 2 is a graph showing the magnitude of chemical or thermal energy binding water and hydrocarbon molecules to the mineral and organic surfaces of the rock as a function of the amount of water and hydrocarbon molecules extracted from the rock.

FIG. 2 shows the pictorial representation of a staircase curve representing increasing levels of energy and molecules of water (top) and hydrocarbons (bottom) attached to the surfaces of the mineral and organic rock constituents at these various levels. These may be van der Waals, capillary, electrical double layer, and other bounding surface forces. Conceptually, one may use different energy levels (thermal or chemical) to extract the oil and water molecules, within these levels. The others will remain bound to the rock.

Figure 3:
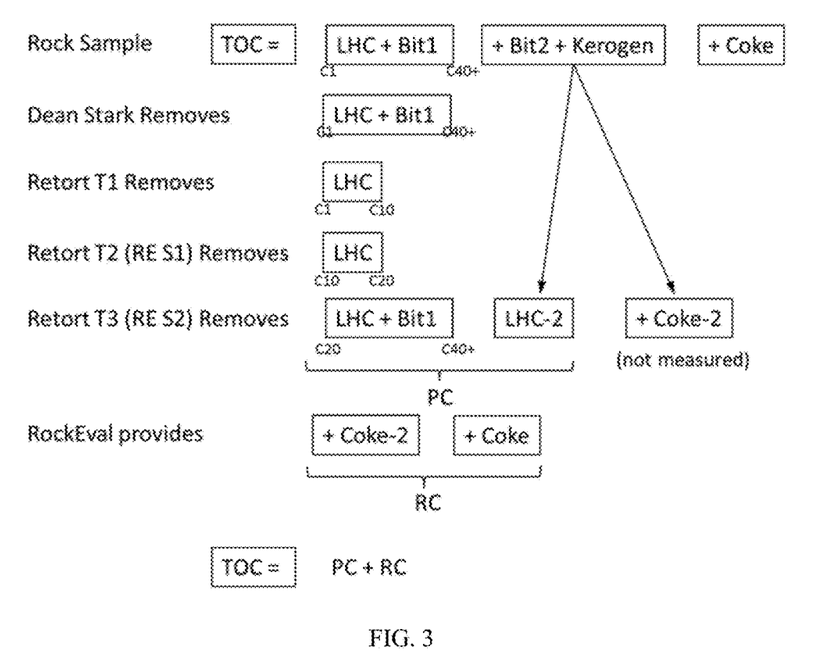
FIG. 3 is a diagram illustrating the components of the total organic carbon (TOC) and the measurements that may be performed to extract these components.

FIG. 3 shows the interpretation of the components of the total organic carbon (TOC) measured in the rock and the components that can be measured by the different methods: LHC represents the liquid hydrocarbon components in the sample (C1 to C40+). Bitumen_1 is the fraction of the bitumen that is easily removable with organic solvents. Bitumen_2 is the fraction of the bitumen that is intrinsically integrated and protected by the host rock and requires removal of the mineral matrix with acids prior to exposure to organic solvents, for extraction (Alexandra Ptaszynska 2015, PhD Thesis, The role of mineral and organic matter constituents in kerogen transformation ratio. Gdansk University of Technology, Faculty of Chemistry, Poland.) Kerogen is the component of the solid organic matter that is insoluble in organic solvents, and that has potential for generating hydrocarbons by thermal cracking, and Coke is the non-soluble residue (dead carbon with no potential for generating hydrocarbons).

The calibration step may be important to ensure that the systems deliver the same thermal or chemical energy to the samples, in order to obtain the same volumes of extracted fluids. However, because of their different design, materials, and thermal properties, slightly different temperatures may be needed to obtain the same thermal energy at the sample. The calibration process accounts for this variability and ensures that once calibrated, the various instruments provide the same extracted volumes for the same samples at their set stages of operation.

Once the various instruments have been referenced and calibrated (using the proper temperature limits, similar temperature ramp rates, and using consistent sample mesh size, and once the solvent extraction and thermal extraction relationships are understood), the following differentiation can be made. Dean Stark, ASE or an equivalent solvent extraction method can be used to quantify all liquid hydrocarbon components including Bitumen_1. Simultaneously, thermal extraction methods (Retort or Thermo Gravimetric Analysis TGA) set at 120° C. are used to extract the light hydrocarbon components (C1 to C10). In practice, this range excludes all the low molecular weight, volatile, hydrocarbon components that have evaporated from the sample at room conditions. However, these can be added to the measurements by understanding the gas-filled porosity and the phase transformation behavior of the mixture. Thermal extraction methods in the range from 120° C. to 300° C., including Rock-Eval analysis (typically known as S1), are used to evaluate the intermediate molecular weight constituents: C10 to C20. Similarly, thermal extraction methods in the range from 300° C. to 650° C., including Rock-Eval analysis (typically known as S2), provide the heavier hydrocarbon components C20 to C40+, generate additional liquid hydrocarbon components (usually light) due to cracking, and also generate non-soluble residue (Coke).

Figure 4:
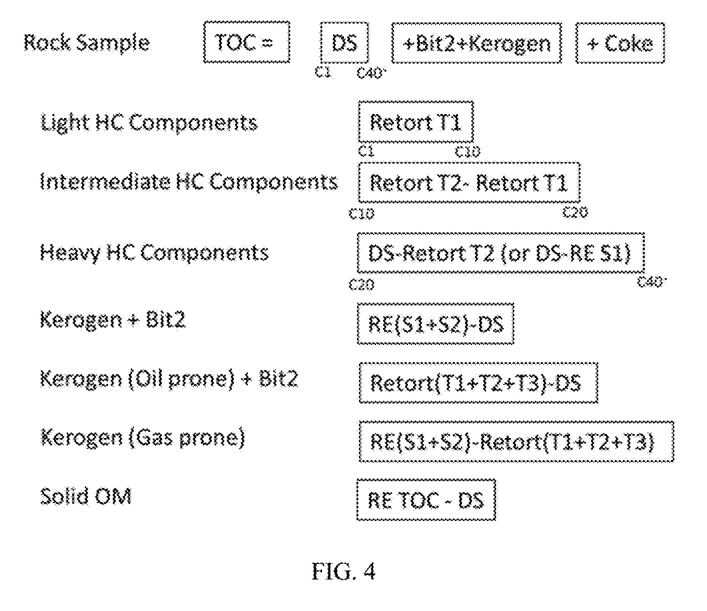
FIG. 4 is a diagram illustrating a workflow that may be used to integrate the measurements shown in FIG. 3 and evaluate the components of the total organic carbon.

FIG. 4 shows similar information, but focusing on the type of measurement that is conducted to obtain the desired hydrocarbon constituent. Clearly, one can obtain light molecular weight hydrocarbon components (C1 to C10), intermediate components (C10 to C20) and heavier ones (C20 to C40+). In addition, one can quantify the amount of solid hydrocarbons in the sample and differentiate kerogen from dead carbon, and further differentiate gas prone kerogen from oil prone kerogen.

Similarly, the various components of the loosely bound water (120° C.), strongly bound water (120° C. to 300° C.), and structural water (300° C. to 650° C.) can be evaluated readily at the various temperatures. This method is well known and is used in our final presentation of results.

FIGS. 5 through 9 provide measurements that validate the method.

Figure 5:
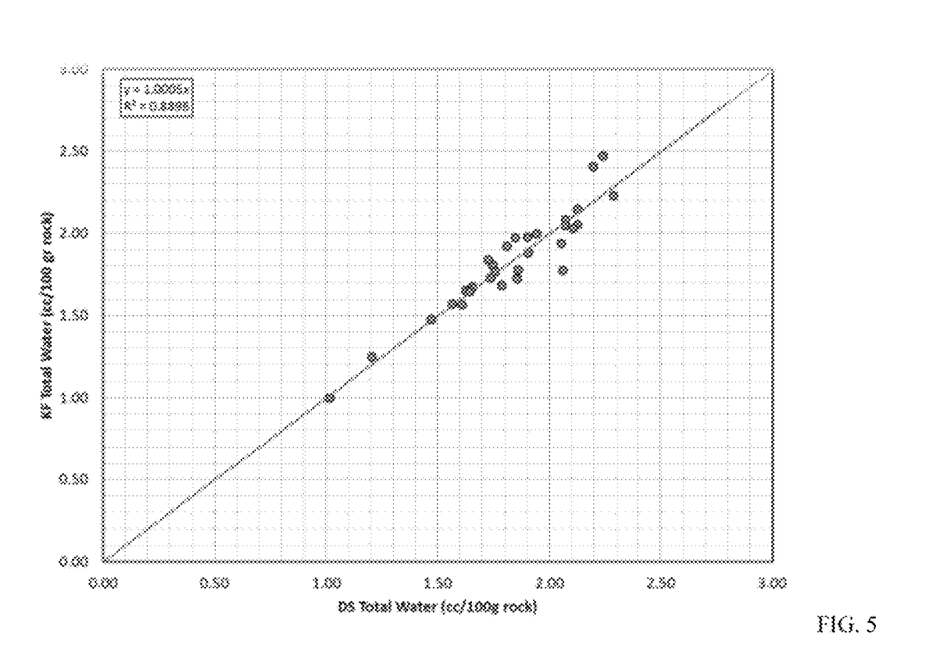
FIG. 5 is a graph illustrating the equivalence between the amounts of extracted water using a first solvent method (Dean Stark) and a second solvent method (Karl Fisher).

FIG. 5 shows a comparison and linear regression of independent measurements of solvent extracted water measured volumetrically via the Dean Stark method and by coulometric titration using the Karl Fisher method. By adjusting the procedures, and residence times, the two methods were set to provide identical results. (Reservoir and non-reservoir unconventional samples were tested. A linear relationship was found with a R^2 value of 0.991)

Figure 6:
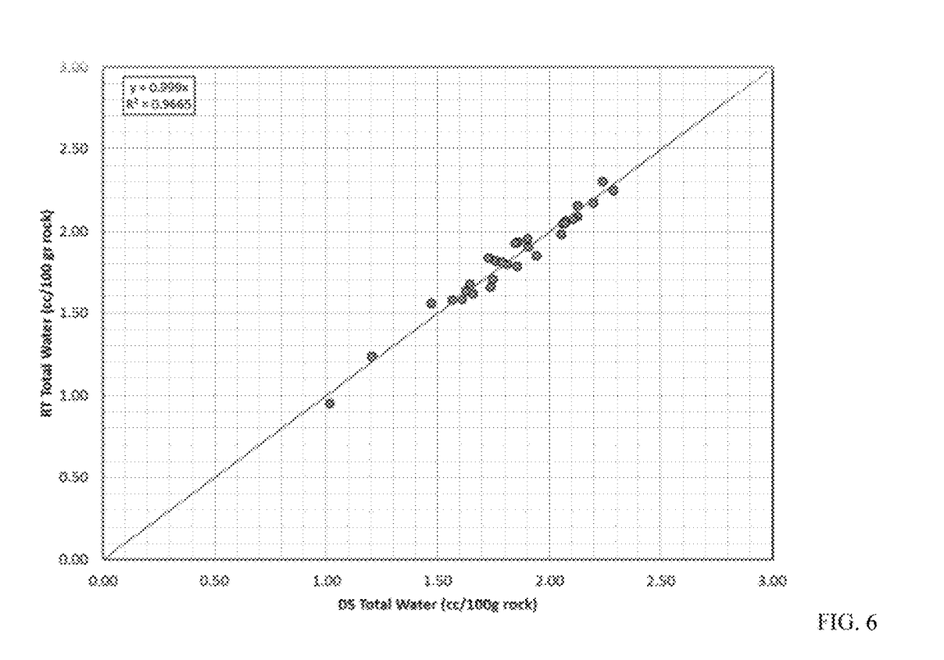
FIG. 6 is a graph illustrating the equivalence between the amounts of extracted water using a solvent method (Dean Stark) method and a thermal method (Retort).

FIG. 6 shows a comparison and linear regression of independent measurements of extracted water via Dean Stark solvent extraction and Retort thermal extraction (at 300° C.). Once again by adjusting the procedures, and residence times, and sieve sizes, the two methods were set to provide identical results. The sieve size (and thus the exposed surface area) was found to directly influence the water exchange (evaporation and condensation) with the environment. In contrast, this was insensitive to the evaporation of hydrocarbons. Thus the sieving size and the sieving procedures are of highest importance for evaluating water content and for maintaining the measurements between instruments consistent.

Figure 7:
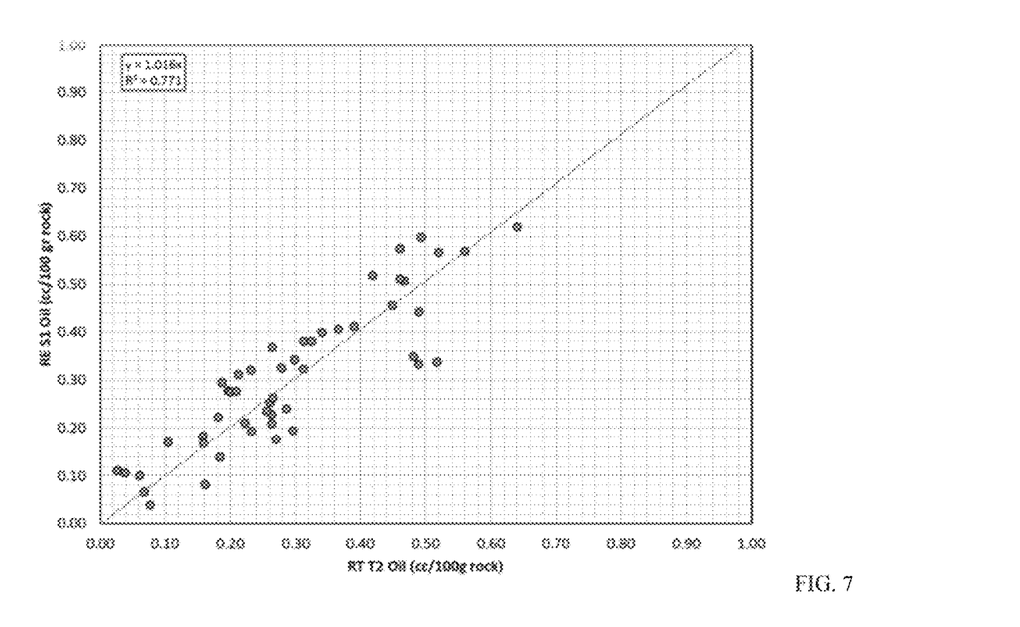
FIG. 7 is a graph illustrating the equivalence between the amounts of extracted hydrocarbons using a first thermal method (Retort) and a second thermal method (Rock-Eval) at a temperature of approximately 300 degrees Celsius.

FIG. 7 shows a comparison and linear regression of independent measurements of thermally extracted intermediate molecular weight hydrocarbon components (at 300° C.) via Retort and Rock-Eval. The measurements are highly correlated with a slope of 1 and a regression coefficient of 0.7. The scatter between measurements is primarily associated with uncertainties due to the small volumes measured. As the volumes increase, the uncertainty decreases and the relationship is more robust. (The Retort measurements of hydrocarbon volume depend on the amount of the vaporized hydrocarbons that are condensed in the measuring probe, and thus on the efficiency of the system to condense most of the vaporized hydrocarbons. The Rock-Eval system measures the vaporized products directly and does not depend on the condensation efficiency).

Figure 8:
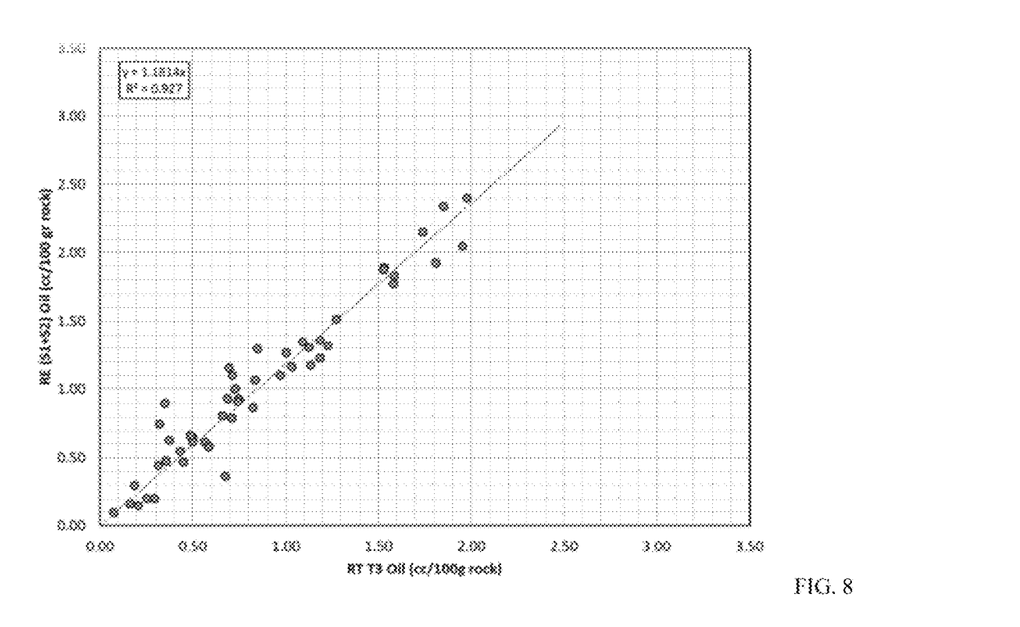
FIG. 8 is a graph illustrating the equivalence between the amounts of extracted hydrocarbons using a first thermal method (Retort) and a second thermal method (Rock-Eval) at a temperature of approximately 650 degrees Celsius for samples with low potential of kerogen conversion.

FIG. 8 shows a comparison and linear regression of independent measurements of thermally extracted high molecular weight hydrocarbon components and converted light molecular components from kerogen cracking (at 60° C.-650° C.) via Retort and Rock-Eval (S1+S2). The measurements are highly correlated with a slope of 1 and a regression coefficient of 0.9. The Rock-Eval measurements are slightly higher than the Retort measurements because, in Rock-Eval, the evaporated products are measured directly (using an IR detector); in Retort, the products are condensed and measured volumetrically. Thus, the latter measurement may introduce small errors due to loss of material. These differences can be further corrected by calibrating the recovery efficiency of the Retort system.

Figure 9:
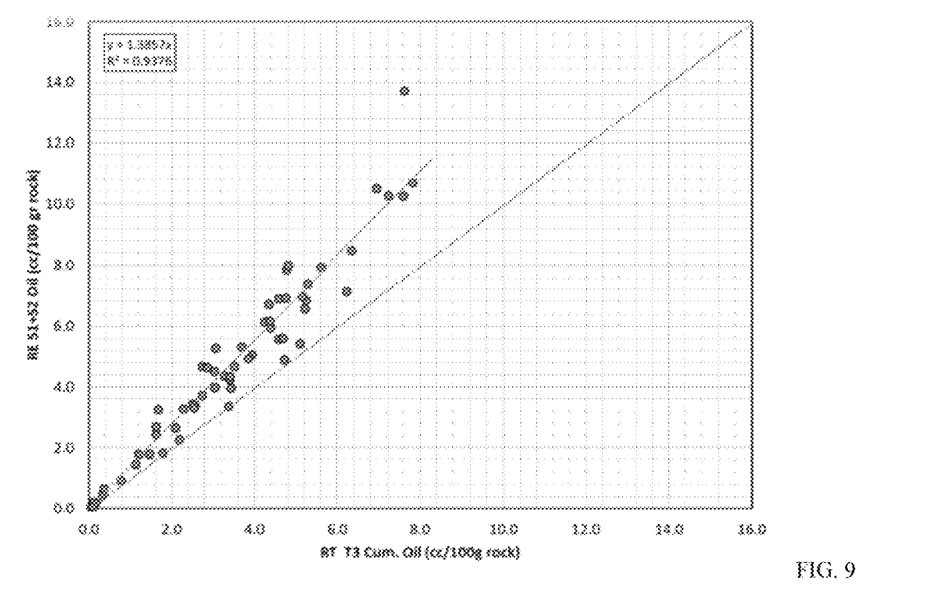
FIG. 9 is a graph illustrating the non-equivalence between the amounts of extracted hydrocarbons using a first thermal method (Retort) and a second thermal method (Rock-Eval) at a temperature of approximately 650 degrees Celsius for samples with higher potential of kerogen conversion that the samples used in the graph of FIG. 8.

FIG. 9 shows an identical comparison as presented in the previous but for a sample with considerably higher kerogen conversion potential. The higher accuracy of the Rock-Eval detectors versus the losses associated with the evaporation and condensation process are observed. These differences are instrument dependent and should be properly evaluated and calibrated, to obtain identical results.

Figure 10:
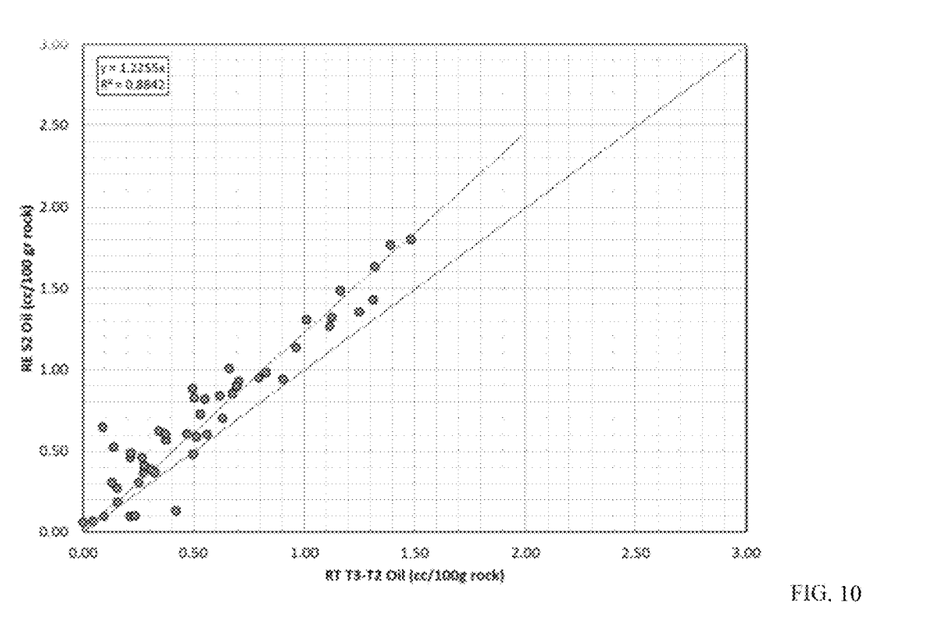
FIG. 10 is a graph illustrating the non-equivalence between the amounts of extracted hydrocarbons using a first thermal method (Retort T3-T2) and a second thermal method (Rock-Eval S2-S1).

FIG. 10 shows a comparison and linear regression of independent measurements of thermally extracted high molecular weight hydrocarbon components and converted light molecular components from kerogen cracking (at 300° C.-650° C.) via Retort (T3-T2) and Rock-Eval (S2). The measurements are strongly correlated with a regression coefficient of 0.88 and are more accurately measured via Rock-Eval.

Figure 11:
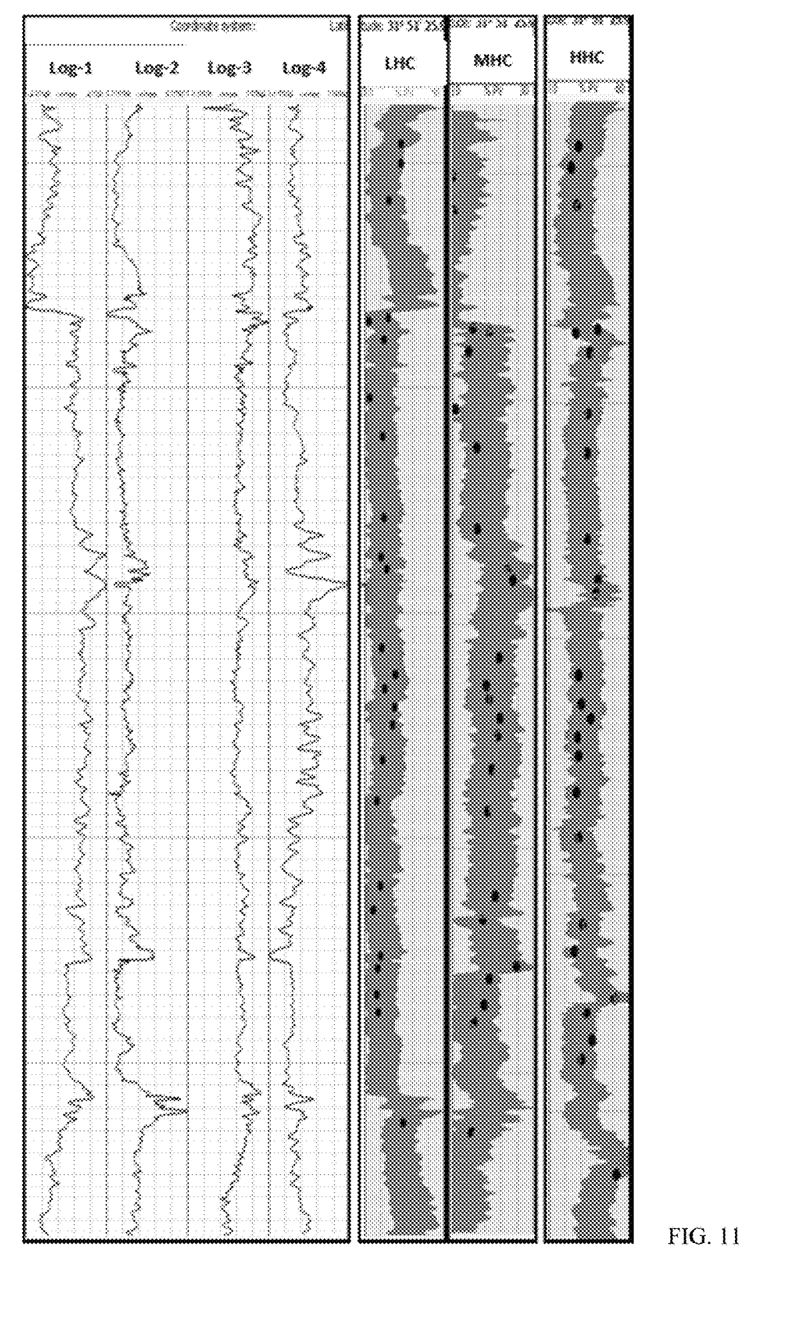
FIG. 11 is a graph showing the amounts of light, medium and heavy hydrocarbons at a plurality of sample locations along a well drilled in a formation and the interpolation of these amounts using logs measured in the well.

FIG. 11 shows a regression between log measurements and the lab measurements, on a rock class by class basis, to propagate the measured values of C1-C10 hydrocarbons, C10-C20 hydrocarbons and C20+ hydrocarbons along the region of interest.

The lab measurements are plotted with as solid black dots on the three tracks on the right of FIG. 11. The lab measurements are fitted to a combination, for example, a linear combination, of the four logs shown on the left of FIG. 11. The logs may be, for example, NMR logs, resistivity logs, or other petrophysical logs. The multivariate fitting model is constructed between the variance of the well logs and the lab measurements and then the fitting model is continuously propagated along the section of the well. The fitting coefficient may be used to predict the lab measurements in a continuous curve along the region of interest. Also shown, the region of uncertainty may also be plotted. Then, fractions of hydrocarbons that are mobile can also be determined using at least the predicted relative amounts of heavier molecular weight components (HC>C20) along the well, and preferably using relative amounts of light molecular weight components (HC<C10) and intermediate molecular weight components (C10<HC<C20). The relative amount of light molecular weight components may always be mobile. The relative amount of heavy molecular weight components may always be non-mobile. The relative amount of intermediate molecular weight may or may not be mobile depending on depth and temperature in the well.

The method of this disclosure may further comprise outputting the prediction results of relative amounts of light, intermediate and heavier molecular weight components, as well as the fractions of hydrocarbons that are mobile. When integrated with mechanical considerations of lateral wellbore placement, such as disclosed in provisional U.S. patent application Ser. No. 62/152,167, the interpolation results provides additional information to supplement the selection of optimal lateral well landing points and improves the provide an additional criterion for selecting optimal landing locations of lateral wells. For example, the selection of optimal landing locations of lateral wells may be based on a combination of low relative content of high molecular weight constituents as well as adequate fracturing connectivity, and indications of good performance of hydraulic fracturing. A higher relative content of high molecular weight constituents is usually associated with more viscous hydrocarbons and thus less mobile hydrocarbons that are more difficult to produce. Further, these results may additionally be integrated with reservoir quality.

Figure 12:
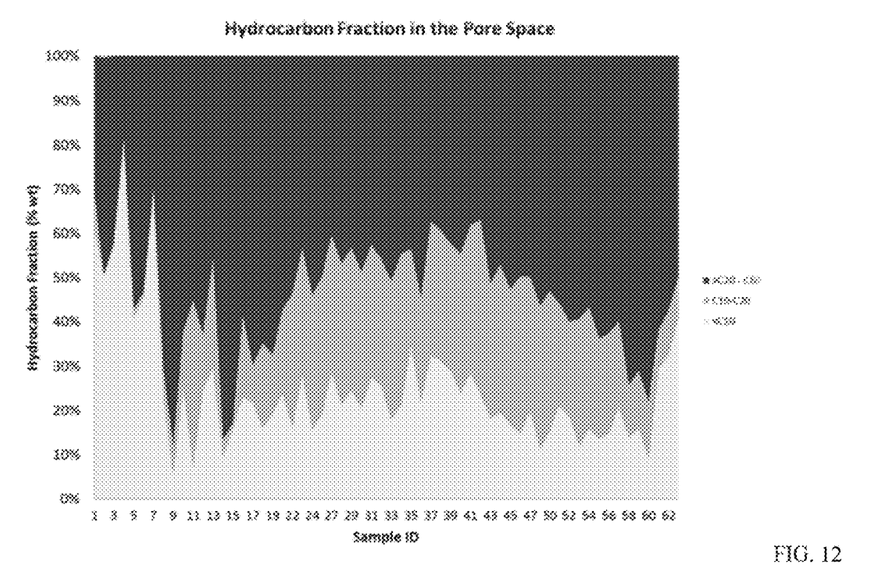
FIG. 12 is a graph showing the relative amounts of light, medium and heavy hydrocarbons at a plurality of sample locations.

FIG. 12 shows the distribution of light, intermediate and high molecular weight hydrocarbon components along the region of interest. Under similar conditions of hydrocarbon filled porosity, the importance and implication of understanding the distribution of the light, intermediate and high-end hydrocarbons is easily seen here. Locations 17 to 56 (x-axis) are associated with the region with high content of light and intermediate molecular weight hydrocarbons, and correspondingly with the higher mobility ones.

Figure 13:
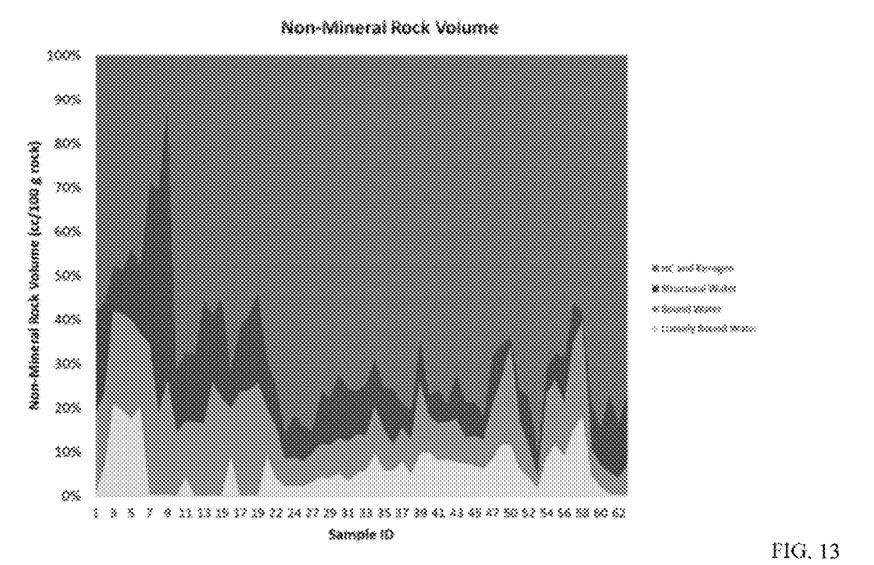
FIG. 13 is a graph showing the relative amounts of loosely bound, bound and structural water as well as liquid hydrocarbons and kerogen at a plurality of sample locations.

FIG. 13 shows the corresponding distribution of pore and matrix waters: loosely bound, strongly bound and structural water.

Figure 14A:
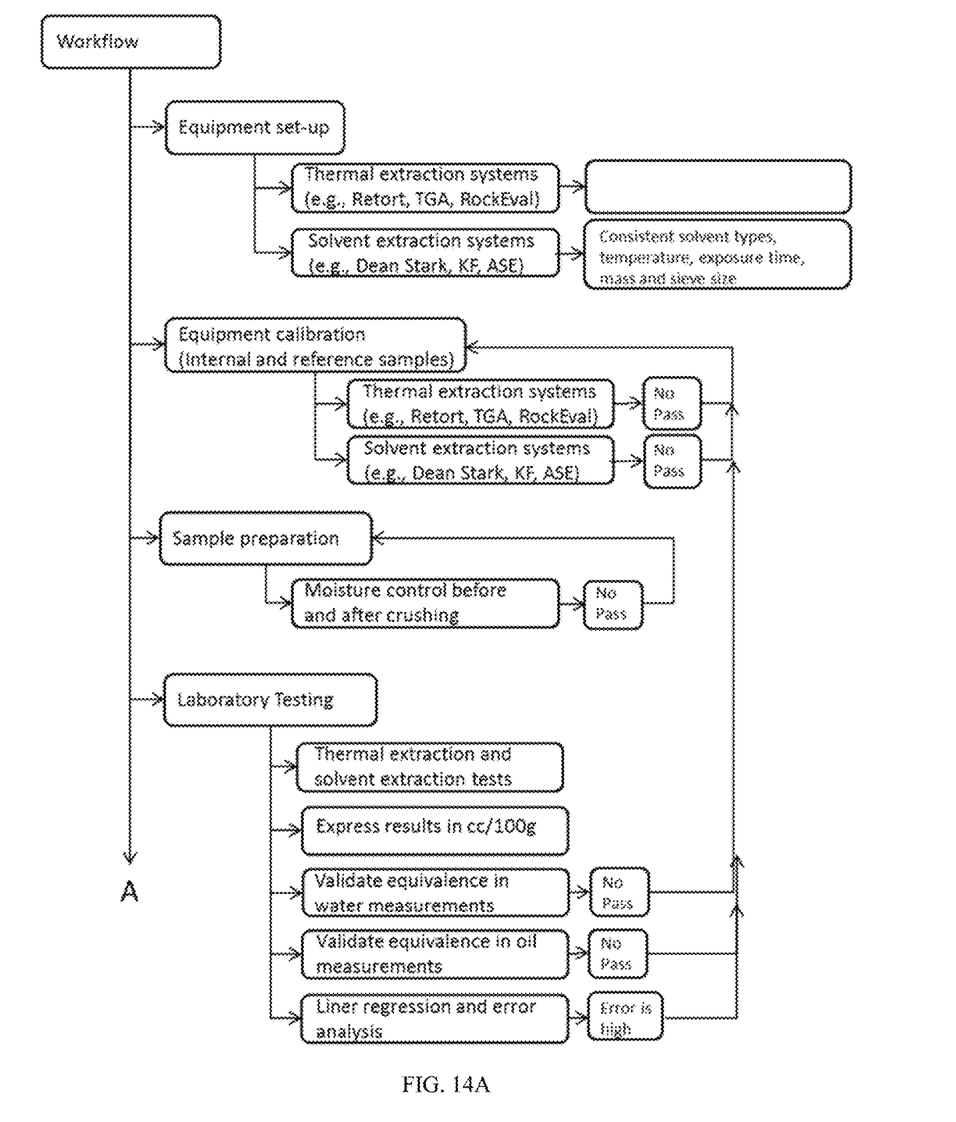
FIGS. 14A-14C are a workflow diagram of a method in accordance with the disclosure.
Figure 14B:
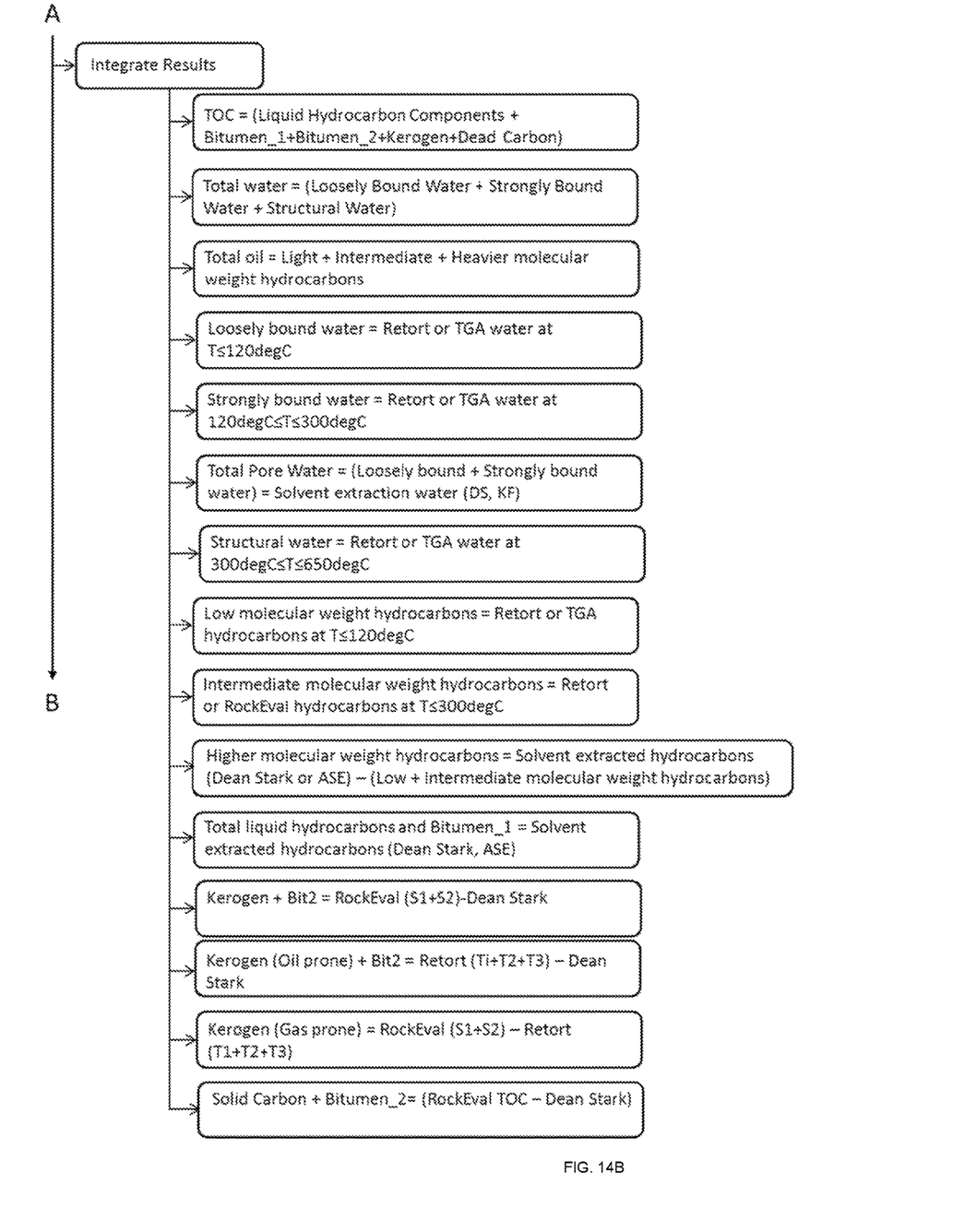
Figure 14C:
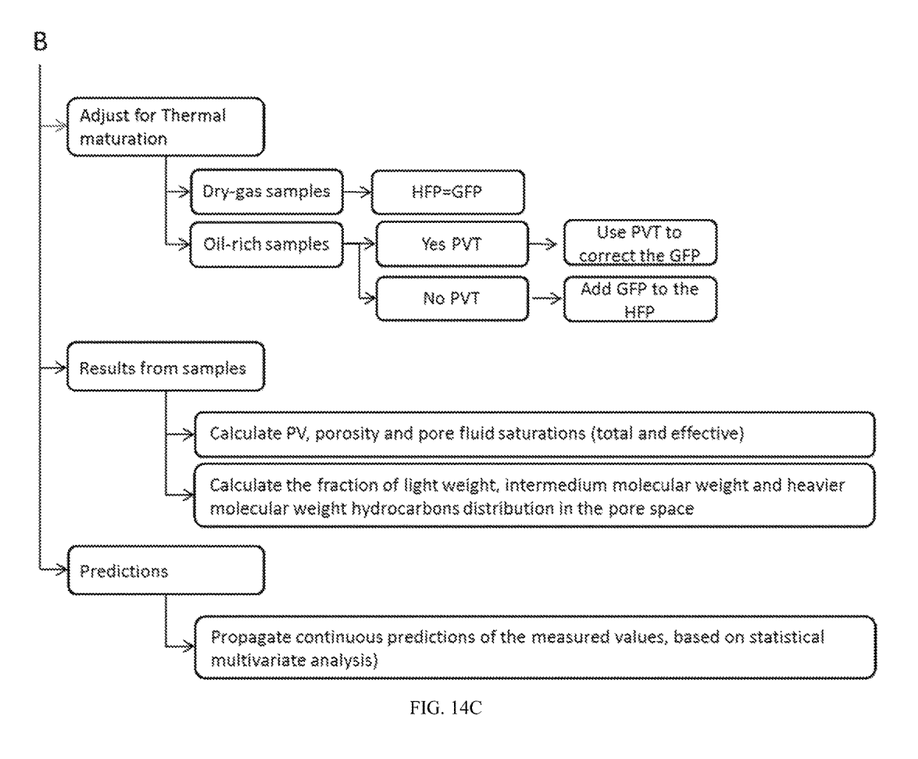

FIGS. 14A-14C show the workflow diagram of the method. It consists of the following:

Equipment Set-Up:
a. Set consistent temperature steps between instruments
b. Set consistent temperature ramp rates between instruments
c. Select solvent types, temperature, solvent schedules and exposure time, for the various instruments
d. For ASE, select the pressure and temperature and exposure time Instruments Calibration
a. Select a common standard for water extraction, oil extraction, and hydrocarbon/kerogen cracking.
b. Calibrate and validate each instrument.

Mass and Sieve Size Requirements
a. Water extraction is strongly sensitive to the temperature schedule, the temperature ramp rate, and the sieve size (the exposed surface area). Thus for water extraction measurements, the sieve size for tests on the various instruments should be similar. The mass requirements depend on the resolution of the measurements.
b. Oil extraction is less sensitive to sieve size, and often one obtains identical results with considerably different sieve sizes and different mass.

Sample Preparation and Moisture Control
a. Substantial variability in the measurements is often associated with water exchange (imbibition or evaporation) during sample storage, handling, preparation, and crushing.
b. Maintain moisture control and preservation at all times, and particularly during crushing.
c. Use environmental control glove-boxes and sealed rock-crushers that are purged with nitrogen gas prior to crushing.

Select Reference Samples for Oil and Water
a. Tight-clean siltstones and mature dry gas mudstone samples are good reference samples for water measurements.
b. Tight-clean siltstones and well-characterized oil-rich mudstones are good reference samples for oil measurements.
c. The selected samples are separated in several portions. Preferably, portions are randomly selected from a crushed and homogenized rock specimen. If the selection is not random, the calibration may be biased.

Conduct Tests on Selected Samples
a. Conduct tests on the various thermal extraction and solvent extraction instruments (e.g., Retort, TGA, Rock-Eval, Dean Stark, Karl Fisher, ASE) using reference samples.
b. Express results from all measurements as extracted volume (in cc) per 100 gr of rock or as fractions of the sample bulk volume, or alternatively as % of the bulk rock volume.
c. Evaluate results and validate the equivalence between water measurements, oil measurements and, solid carbon measurements, at the corresponding temperature limits: For example, the extracted water using the Retort method at the first temperature stage (300 deg C.) should be the same as the extracted water using TGA at the first temperature stage (which may be slightly different than 300 deg C.), and the same as the corresponding water extracted with solvents (Dean Stark, Karl Fischer, ASE). Similarly, the extracted oil using the Retort method at the first temperature stage should be the same as the extracted oil using Rock-Eval at the same temperature of 300 deg C., even though the first temperature stage of the retort system may be slightly different than 300 deg C.
d. Evaluate the relationship between the above using a linear fit regression, define the confidence interval and conduct error propagation analysis Use the above results and calibrations to define an integrated evaluation of reservoir properties, using the following model:

a. Organic carbon: TOC=(Liquid Hydrocarbon Components Bitumen_1+Bitumen_2+Kerogen+Dead Carbon)
b. Water: Total water=(Loosely Bound Water+Strongly Bound Water+Structural Water).
c. Oil: Light molecular weight hydrocarbons (C1-C10)+Intermediate molecular weight hydrocarbons (C10-C20)+Heavier molecular weight hydrocarbons including bitumen (>C20)
d. Loosely bound water=Retort or TGA water at T≤120 deg C.
e. Strongly bound water=Retort or TGA water at 120 deg C.≤T≤300 deg C.
f. Total Pore Water=(Loosely bound+Strongly bound water)=Solvent extraction water: Dean Stark water or Karl Fischer water
g. Structural water=Retort or TGA water at 300 deg C.≤T≤650 deg C.
h. Low molecular weight hydrocarbons=Retort or TGA hydrocarbons at T≤120 deg C.
i. Intermediate molecular weight hydrocarbons=Retort or Rock-Eval hydrocarbons at T≤300 deg C.
j. Higher molecular weight hydrocarbons=Solvent extracted hydrocarbons (Dean Stark, ASE)−(Low+Intermediate molecular weight hydrocarbons)
k. Total liquid hydrocarbons including Bitumen_1=Solvent extracted hydrocarbons (Dean Stark, ASE)
l. Oil Prone Kerogen+Bitumen_2=(Retort Oil T≤650 deg C.−Dean Stark Oil).
m. Oil and Gas Prone Kerogen+Bitumen_2=(Rock-Eval Oil T≤650 deg C.−Dean Stark Oil).
n. Gas Prone Kerogen=(Rock-Eval Oil T≤650 deg C.−Retort Oil T≤650 deg C.).
o. Solid Carbon+Bitumen_2=(Rock-Eval TOC−Dean Stark)

If the results do not agree with the specified relationships, return to calibration and sample preparation specifications. For example, the total pore water amount may be compared with the sum of the loosely bound water amount and the strongly bound water amount, and in cases of disagreement, another sample may be prepared.

Effect of Thermal Maturation
a. For thermally-mature, dry-gas samples, the hydrocarbon-filled porosity is equal to the gas-filled porosity and the above evaluation is conducted for pore-water assessment exclusively.

b. For oil-rich-samples, some of the liquid hydrocarbons present at reservoir pressure and temperature transform into gas at laboratory conditions. PVC phase transformation analysis allows reconciling the two. In the absence of this, it is customary to assume that at reservoir conditions the hydrocarbon in place is single phase and liquid. Thus, the gas-filled porosity is added to the liquid-hydrocarbon-filled porosity to evaluate the hydrocarbon-filled porosity.

Calculate the total pore volume the corresponding porosity (effective and total) and the pore fluid saturations (effective and total).

Calculate the fraction of light weight, intermedium molecular weight, and heavier molecular weight hydrocarbons distribution in the pore space.

When samples are selected based on similar core-log responses, obtained at cm-resolution, the analysis helps breaking down a heterogeneous system in their similar (more homogeneous) constituents. In this case, each rock class is characterized in detail, as indicated above, and a model is created between their measured properties and the bulk core-logger responses that define their behavior. In this case, the model can be propagated, and continuous properties are provided along the core length.

Although a few example embodiments have been described in detail above, those skilled in the art will readily appreciate that many modifications are possible in the example embodiments without materially departing from this disclosure. Accordingly, such modifications are intended to be included within the scope of this disclosure as defined in the following claims. In the claims, means-plus-function clauses are intended to cover the structures described herein as performing the recited function and not simply structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:
   conducting first calibration measurements on a first subset of reference samples of porous rock having water and hydrocarbon fluids in the pores with a thermal extraction instrument operated at temperature limits, wherein the thermal extraction instrument is selected from the group consisting of Retort, Thermo Gravimetric Analysis (TGA), and Rock-Eval;
   conducting second calibration measurements on a second subset of the reference samples of porous rock having water and hydrocarbon fluids in the pores with a solvent extraction instrument, wherein the solvent extraction instrument is selected from the group consisting of Dean Stark, Karl Fisher, and Accelerated Solvent Extraction (ASE);
   calibrating the temperature limits at which the thermal extraction instrument operates to validate an equivalence between at least one of water measurements, oil measurements, and solid carbon measurements derived from the first calibration measurements, and a corresponding one of water measurements, oil measurements, and solid carbon measurements derived from the second calibrations measurements;
   conducting a first measurement with the thermal extraction instrument using the calibrated temperature limits on a first portion of a sample of porous rock having water and hydrocarbon fluids in the pores;
   conducting a second measurement with the solvent extraction instrument on a second portion of the sample of porous rock; and
   evaluating a component amount in the porous rock from the first and second measurements, wherein the component is one of heavier molecular weight hydrocarbons having at least 20 carbon atoms, oil prone kerogen+bitumen_2, oil and gas prone kerogen+bitumen_2, and solid carbon+bitumen_2.

2. The method of claim 1 further comprising:
   evaluating a loosely bound water amount in the sample of porous rock using a measurement conducted with the thermal extraction instrument using one of the calibrated temperature limits, a strongly bound water amount in the sample of porous rock using a measurement conducted with the thermal extraction instrument using another one of the calibrated temperature limits, and a total pore water amount in the sample of porous rock using a measurement conducted with the solvent extraction instrument.

3. The method of claim 1 further comprising:
   evaluating amounts of light molecular weight components having less than 10 carbon atoms, intermediate molecular weight components having at least 10 and less than 20 carbon atoms, and heavier molecular weight components having at least 20 carbon atoms in the sample of porous rock.

4. The method of claim 1 further comprising:
   performing a regression between amounts of heavier molecular weight components having at least 20 carbon atoms evaluated in several samples of porous rock taken along a well, and well log values at locations where the several samples of porous rock have been taken;
   predicting, using the regression, relative amounts of heavier molecular weight components having at least 20 carbon atoms along the well;
   determining fractions of hydrocarbons that are mobile using at least the predicted relative amounts of heavier molecular weight components having at least 20 carbon atoms along the well; and
   selecting an optimal landing location for a lateral well based on the fractions of hydrocarbons that are mobile and indications of performance of hydraulic fracturing.

5. A method, comprising:
   conducting first calibration measurements on a first subset of reference samples of porous rock having water and hydrocarbon fluids in the pores with a first thermal extraction instrument operated at first temperature limits, wherein the first thermal extraction instrument is selected from the group consisting of Retort, Thermo Gravimetric Analysis (TGA), and Rock-Eval;
   conducting second calibration measurements on a second subset of the reference samples of porous rock having water and hydrocarbon fluids in the pores with a solvent extraction instrument, wherein the solvent extraction instrument is selected from the group consisting of Dean Stark, Karl Fisher, and Accelerated Solvent Extraction (ASE);
   calibrating the first temperature limits at which the first thermal extraction instrument operates to validate a first equivalence between at least one of water measurements, oil measurements, and solid carbon measurements derived from the first calibration measurements, and a corresponding one of water measurements, oil measurements, and solid carbon measurements derived from the second calibrations measurements;

conducting third calibration measurements on a third subset of the reference samples of porous rock having water and hydrocarbon fluids in the pores with the first thermal extraction instrument operated at the first calibrated temperature limits;

conducting fourth calibration measurements on a fourth subset of the reference samples of porous rock having water and hydrocarbon fluids in the pores with a second thermal extraction instrument operated at second temperature limits, wherein the second thermal extraction instrument is selected from the group consisting of Retort, TGA, and Rock-Eval, and wherein the second thermal extraction instrument is different from the first thermal extraction instrument;

calibrating the second temperature limits at which the second thermal extraction instrument operates to validate a second equivalence between at least one of water measurements, oil measurements, and solid carbon measurements derived from the fourth calibration measurements, and a corresponding one of water measurements, oil measurements, and solid carbon measurements derived from the third calibrations measurements;

conducting a first measurement with the first thermal extraction instrument using the first calibrated temperature limits on a first portion of a sample of porous rock having water and hydrocarbon fluids in the pores;

conducting a second measurement with the solvent extraction instrument on a second portion of the sample of porous rock;

conducting a third measurement with the second thermal extraction instrument using the second calibrated temperature limits on a third portion of the sample of porous rock having water and hydrocarbon fluids in the pores; and evaluating a component amount in the porous rock from the first, second, and third measurements, wherein the component is one of hydrocarbons having at least 20 carbon atoms, oil prone kerogen+bitumen_2, oil and gas prone kerogen+bitumen_2, and solid carbon+bitumen_2.

6. The method of claim 5,
wherein the component is oil prone kerogen+bitumen_2.
7. The method of claim 5,
wherein the component is oil and gas prone kerogen+bitumen_2.
8. The method of claim 5,
wherein the component is solid carbon+bitumen_2.

9. The method of claim 5 further comprising:
performing a regression between amounts of heavier molecular weight components having at least 20 carbon atoms evaluated in several samples of porous rock taken along a well, and well log values at locations where the several samples of porous rock have been taken;

predicting, using the regression, relative amounts of heavier molecular weight components having at least 20 carbon atoms along the well;

determining fractions of hydrocarbons that are mobile using at least the predicted relative amounts of heavier molecular weight components having at least 20 carbon atoms along the well; and selecting an optimal landing location for a lateral well based on the fractions of hydrocarbons that are mobile and indications of performance of hydraulic fracturing.

10. A method, comprising:
conducting first calibration measurements on a first subset of reference samples of porous rock having water and hydrocarbon fluids in the pores with a first thermal extraction instrument operated at temperature limits, wherein the first thermal extraction instrument includes one of-Retort, Thermo Gravimetric Analysis (TGA), and Rock-Eval;

conducting second calibration measurements on a second subset of the reference samples of porous rock having water and hydrocarbon fluids in the pores with a second thermal extraction instrument, wherein the second thermal extraction instrument includes one of Retort, TGA, and Rock-Eval, and wherein the second thermal extraction instrument is different from the first thermal extraction instrument;

calibrating the temperature limits at which the first thermal extraction instrument operates to validate an equivalence between at least one of water measurements, oil measurements, and solid carbon measurements derived from the first calibration measurements, and a corresponding one of water measurements, oil measurements, and solid carbon measurements derived from the second calibrations measurements;

conducting a first measurement with the first thermal extraction instrument using the calibrated temperature limits on a first portion of a sample of porous rock having water and hydrocarbon fluids in the pores;

conducting a second measurement with the second thermal extraction instrument on a second portion of the sample of porous rock; and evaluating a component amount in the porous rock from the first and second measurements, wherein the component is gas prone kerogen.

* * * * *